(12) United States Patent
Iinuma

(10) Patent No.: US 6,669,365 B2
(45) Date of Patent: Dec. 30, 2003

(54) APPARATUS FOR X-RAY FLUOROSCOPY AND RADIOGRAPHY

(75) Inventor: Masao Iinuma, Ibaraki (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 10/106,174

(22) Filed: Mar. 26, 2002

(65) Prior Publication Data
US 2002/0141539 A1 Oct. 3, 2002

(30) Foreign Application Priority Data
Mar. 29, 2001 (JP) ........................................ 2001-094503

(51) Int. Cl.[7] ................................................. H05G 1/02
(52) U.S. Cl. ........................ 378/195; 378/196; 378/206
(58) Field of Search ................................. 378/195, 196, 378/209, 206

(56) References Cited

U.S. PATENT DOCUMENTS

| | | | |
|---|---|---|---|
| 3,702,935 A | * 11/1972 | Carey et al. | 250/58 |
| 3,971,949 A | * 7/1976 | Brather et al. | 250/446 |
| 4,503,552 A | * 3/1985 | Miyahara et al. | 378/196 |
| 5,570,409 A | 10/1996 | Yamaguchi et al. | |
| 6,220,752 B1 | * 4/2001 | Csikos et al. | 378/197 |

FOREIGN PATENT DOCUMENTS

EP  0 444 677 A2  9/1991

* cited by examiner

Primary Examiner—Edward J. Glick
Assistant Examiner—Irakli Kiknadze
(74) Attorney, Agent, or Firm—Rankin, Hill, Porter & Clark LLP

(57) ABSTRACT

A support column holds an X-ray tube having a collimator and is held by a linear guide on a side of a main frame and moved in the longitudinal direction of a table top board by a motor via a gear and a rack. An image receiving system to hold an image intensifier is supported by a linear guide on a side of the main frame and moved in the longitudinal direction of the table top board by a drive mechanism independently from the support column. The table top board can be moved to a position close to the support column on an upper portion of the main frame. When the support column is moved in the longitudinal direction, it is possible for an operator to approach a subject person from an back side portion of the table top board while the operator is being kept in an easy body orientation.

16 Claims, 3 Drawing Sheets

APPARATUS FOR X-RAY FLUOROSCOPY AND RADIOGRAPHY

BACKGROUND OF THE INVENTION

1. Field of the Invention

The present invention relates to an X-ray fluoroscopic and radiographic apparatus. More particularly, the present invention relates to an over-tube type X-ray fluoroscopic and radiographic apparatus in which an X-ray tube and an image receiving system are moved in a longitudinal direction of a table top board.

2. Description of the Related Art

A remote operation type fluoroscopic and radiographic apparatus is mainly used for an inspection of an upper digestive organs in which an X-ray inspection of a stomach portion is mainly executed. The remote operation type fluoroscopic and radiographic apparatus is also used as a multiple-purpose radiographic apparatus for the enema (large intestine), urinary organs, thoracoscope inspection and nerve system.

For this object, especially the over-tube type fluoroscopic and radiographic apparatus is used in which the X-ray tube is located above the table top board, and the spot radiographic device and imaging system are located under the table top board. The reason why the over-tube type fluoroscopic and radiographic apparatus is used will be described as follows. Since the X-ray tube is located at a position distant from the table top board, a large space is formed above the table top board, so that a subject person to be examined can be easily observed and further a body orientation of the subject person can be easily changed. Further, since it is unnecessary for an operator to pay much attention to interference between the subject person and the X-ray tube when the apparatus is operated, operation can be easily performed and a diagnosis efficiency can be enhanced. Furthermore, the apparatus is designed so that a heavy spot radiographic device can be held on a back of the table top board. Therefore, no oppressive sensation is given to the subject person.

The over-tube type fluoroscopic and radiographic apparatus has a large upper space on the table top board. Therefore, in the case where various diagnoses are made on the subject person, for example, in the case where myelography (nervous system) or IVR is conducted, it is possible to make another diagnosis at the same time, for example, an endoscope diagnosis or ultrasonic wave diagnosis can be made at the same time.

FIG. 3 is a side view showing an over-tube type X-ray fluoroscopic and radiographic apparatus which is set in a horizontal posture. A X-ray tube 1 is held by a support column 3. An image receiving system 5 (spot radiographic device and image intensifier 6), is arranged on a back of a table top board 7. The X-ray tube 1 and image receiving system 5 are held by a main frame (not shown) arranged on an upper side of a leg 8 of the fluoroscopic and radiographic apparatus. The X-ray tube 1 and image receiving system 5 are arranged so that they can be moved in a longitudinal direction (they can be moved to position A or B) of the table top board 7. On the other hand, the table top board 7 can be moved in the longitudinal and a lateral direction thereof. The fluoroscopic and radiographic apparatus can be tilted by an angle from 90° (vertical posture) to −45° (reversely oblique posture). It is possible to change a distance from the focus of the X-ray tube 1 to the image receiving system 5 by 110 to 150 cm when a position of the X-ray tube 1 is moved vertically upward and downward. A collimator 2 is of both the remote and the proximity control type. According to the field of view, the collimator 2 can be changed over between the remote and the proximity control type.

FIG. 4 is a sectional view showing an X-ray fluoroscopic and radiographic apparatus which is set in a horizontal posture, wherein this view is taken from a side of an end portion of the X-ray fluoroscopic and radiographic apparatus. The support column 3 supports the X-ray tube 1 and collimator 2. The image receiving system 5 holds the image intensifier 6, which is an image receiving device. The support column 3 and image receiving system 5 are mechanically connected with each other and held being capable of moving in the longitudinal direction of the table top board 7 via a linear guide 10 while the support column 3 is mounted on an upper face of the main frame 4. The main frame 4 can be rotated round a rotary shaft 12 arranged in the leg 8, which is a base, so that the fluoroscopic and radiographic apparatus can be tilted.

Although the related art X-ray fluoroscopic and radiographic apparatus is composed as described above, the following problems may be encountered. The support column 3 for supporting the X-ray tube 1 and the image receiving system 5 are mechanically connected with each other and held being mounted on the upper face of the main frame 4. They are driven in the longitudinal direction of the table top board 7. Therefore, when the table top board 7 is moved to a back side of the apparatus (that is, the right-hand side in FIG. 4), it can be moved only to a position at which the table top board 7 is not contacted with the support column 3. In this case, a portion of the main frame 4 protrudes to a more back side of the apparatus than the table top board 7. Therefore, when an operator approaches the table top board 7 from the back side of the apparatus, a position where the operator is located is too distant from the table top board 7. Therefore, it is difficult for the operator to make a diagnosis for the subject person 11.

SUMMARY OF THE INVENTION

The present invention has been accomplished to solve the above problems. It is an object of the present invention to provide an X-ray fluoroscopic and radiographic apparatus by which a distance from an operator to a table top board is reduced so that a diagnosis can be easily made for a subject person when the operator approaches the subject person, who is put on the table top board, from a backside of the X-ray fluoroscopic and radiographic apparatus.

In order to accomplish the above object, the present invention provides an X-ray fluoroscopic and radiographic apparatus comprising:

a table top board;

a support column for holding an X-ray tube above the table top board;

an image receiving system for holding an image receiving device and being placed on a back of the table top board;

a main frame for holding the support column and the image receiving system so that the support column and the image receiving system can be moved in a longitudinal direction of the table top board, wherein the support column is mechanically held on a side of the main frame which is opposite to a side on which the image receiving system is held.

In the above-mentioned X-ray fluoroscopic and radiographic apparatus, it is preferable that the support column and the image receiving system are mechanically independently held and moved on both sides of the main frame.

Further, in the above-mentioned X-ray fluoroscopic and radiographic apparatus, the support column is held by a linear guide formed on the side of the main frame.

The X-ray fluoroscopic and radiographic apparatus of the present invention is composed as described above. The support column for holding the X-ray tube is mechanically held and moved on a side of the main frame, which is opposite to a side on which the image receiving system is attached. Alternatively, the support column for holding the X-ray tube and the image receiving system for holding the image receiving device on the back of the table top board are respectively independently held on both sides of the main frame. Therefore, the X-ray tube and the image receiving system are independently moved in the longitudinal direction of the table top board, and this movement is made when the support column is held by the linear guide formed on the side of the main frame. Since the support column for holding the X-ray tube is held on the side of the main frame, when the support column is moved in the longitudinal direction of the table top board, a space occupied by the support column becomes open. Further, the table top board can be moved above the main frame, that is, the back side portion of the table top board can be moved to a position close to the support column at an end of the main frame. Therefore, it is possible for the operator to come close to an end of the table top board and make a diagnosis easily for the subject person.

DETAILED DESCRIPTION OF THE INVENTION

Figure 1A:
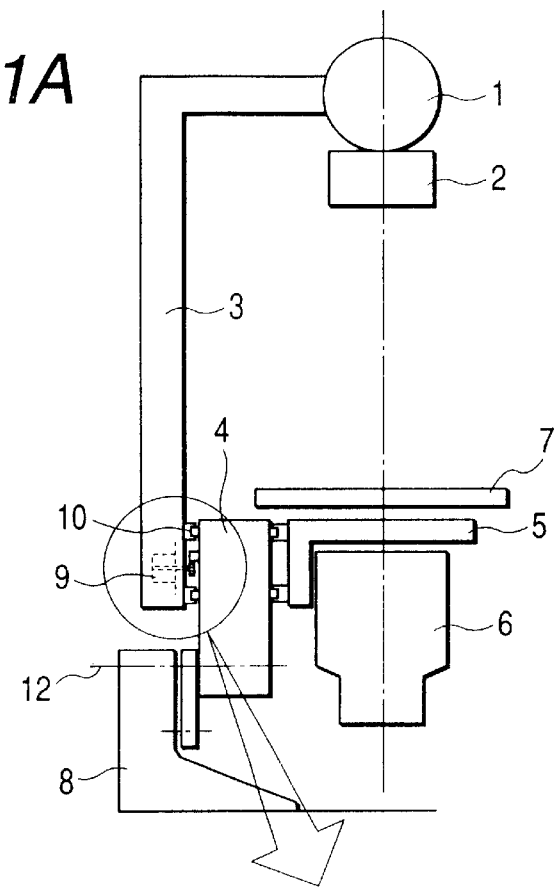
FIGS. 1A and 1B are views showing an embodiment of an X-ray fluoroscopic and radiographic apparatus of the present invention.
Figure 1B:
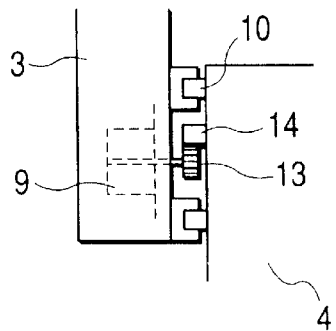
Figure 1C:
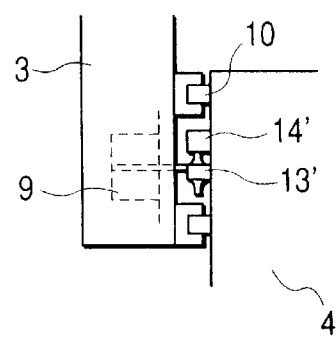
FIG. 1C is a view showing another example of a drive mechanism of the X-ray fluoroscopic and radiographic apparatus of the present invention.

Referring to FIGS. 1A and 1B, an embodiment of the X-ray fluoroscopic and radiographic apparatus of the present invention will be explained below. FIG. 1A is a sectional view of the X-ray fluoroscopic and radiographic apparatus of the present invention which is set at a horizontal posture, wherein the view is taken on the side from an end of the X-ray fluoroscopic and radiographic apparatus. FIG. 1B is a view showing a support mechanism of a support column 3 for supporting a X-ray tube 1 and a collimator 2. The X-ray fluoroscopic and radiographic apparatus includes an X-ray tube 1, a table top board 7, an image receiving system 5, and a main frame 4. The X-ray tube 1 is supported by the support column 3 and provided with the collimator 2. A subject person is put on the table top board 7. The image receiving system 5 holds an image intensifier 6, which is an image receiving device, and is placed on a back of the table top board 7. The main frame 4 is connected with a rotary shaft 12 of a leg 8 which is a base of the apparatus so as to tilts the fluoroscopic and radiographic apparatus. The main frame 4 independently and mechanically holds the support column 3 and the image receiving system 5 on both sides. The X-ray fluoroscopic and radiographic apparatus also includes a drive mechanism (motor 9, gear 13, rack 14 and so forth) for driving the support column 3 along the main frame 4 on the linear guide 10 in the longitudinal direction of the table top board 7, and a drive mechanism (not shown) for driving the image receiving system 5 along the main frame 4 on the linear guide 10 in the longitudinal direction of the table top board 7. The drive mechanism for the image receiving system 5 may comprise a motor 9, a chain 14', and a sprocket 13' as shown in FIG. 1C.

On the X-ray fluoroscopic and radiographic apparatus, the support column 3 for supporting the X-ray tube 1 and collimator 2 is supported on a side of the main frame 4. As shown in FIG. 1B, the supporting mechanism is composed in such a manner that the support column 3 is attached to the side of the main frame 4 via the linear guide 10. A gear 13 is rotated by the power of a motor 9 and meshed with a rack 14 arranged in the main frame 4, so that the support column 3 can be moved in the longitudinal direction of the table top board 7. The image receiving system 5 for holding the image intensifier 6, which is an image receiving device, is attached to a side of the main frame 4, which is opposite to the side on which the support column 3 is attached, via the linear guide 10.

The image receiving system 5 is moved in the longitudinal direction of the table top board 7 independently from the support column 3 by the drive mechanism (not shown) such as a motor, gear, rack and so forth. The drive mechanism may comprises a motor, a chain, and a sprocket. On an upper face of the main frame 4, there is provided a table top board 7 on which a subject person 11 is put. This table top board 7 can be moved longitudinally and laterally on a plane independently from the movement of the X-ray tube 1 and receiving system 5. When the table top board 7 is moved on a back side of the apparatus (that is, the right-hand side in FIG. 1A) so as to place a position close to the support column 3 above the main frame 4 and the support column 3 for supporting the X-ray tube 1 is moved in the longitudinal direction of the table top board 7, a space occupied by the support column 3 becomes open. Therefore, the operator can approach a position very close to the table top board 7. The main frame 4 is connected with and supported by the rotary shaft 12 arranged in an upper portion of the leg which is supported on the floor. Therefore, the fluoroscopic and radiographic apparatus can be tilted round the rotary shaft 12.

The linear guide 10 is a guide for supporting the support column 3 and image receiving system 5 and moving the support column 3 and image receiving system 5 in the longitudinal direction of the table top board 7 with high accuracy. Examples of the linear guide 10 are a rolling guide, sliding guide and magnetic levitation guide. In the embodiment shown in FIG. 1A, a sliding guide is used for the linear guide 10. In the sliding guide shown in FIG. 1, a self-lubrication type or a dry type (no-lubricant type) sliding guide, in which no lubricant is supplied as boundary lubrication, is used. However, it is possible to use either a rail type rolling guide (ball type or roller type), a circular shaft type guide, a flat plate type guide or a follower bearing assembly type guide.

Figure 2A:
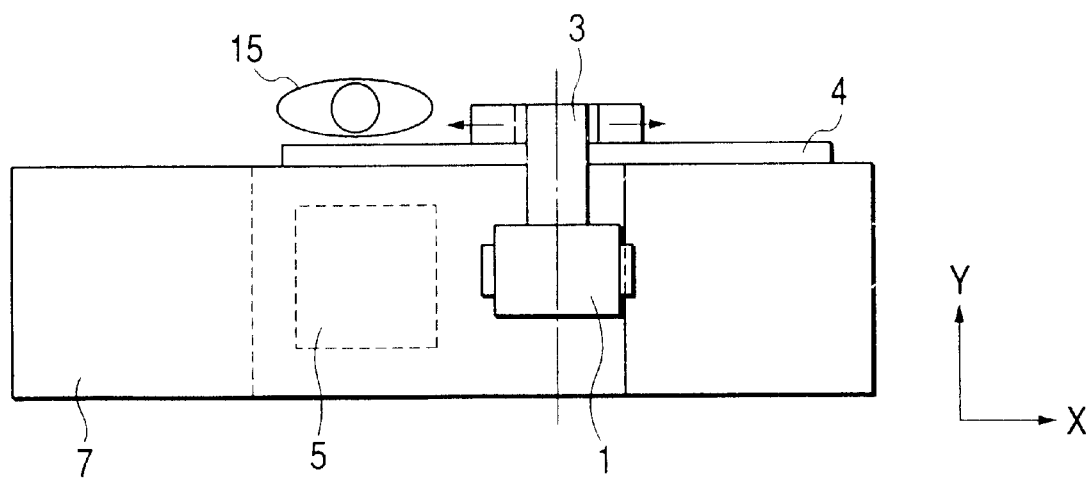
FIG. 2A is an upper face view showing a state in which an operator approaches from a backside of the X-ray fluoroscopic and radiographic apparatus of the present invention.
Figure 2B:
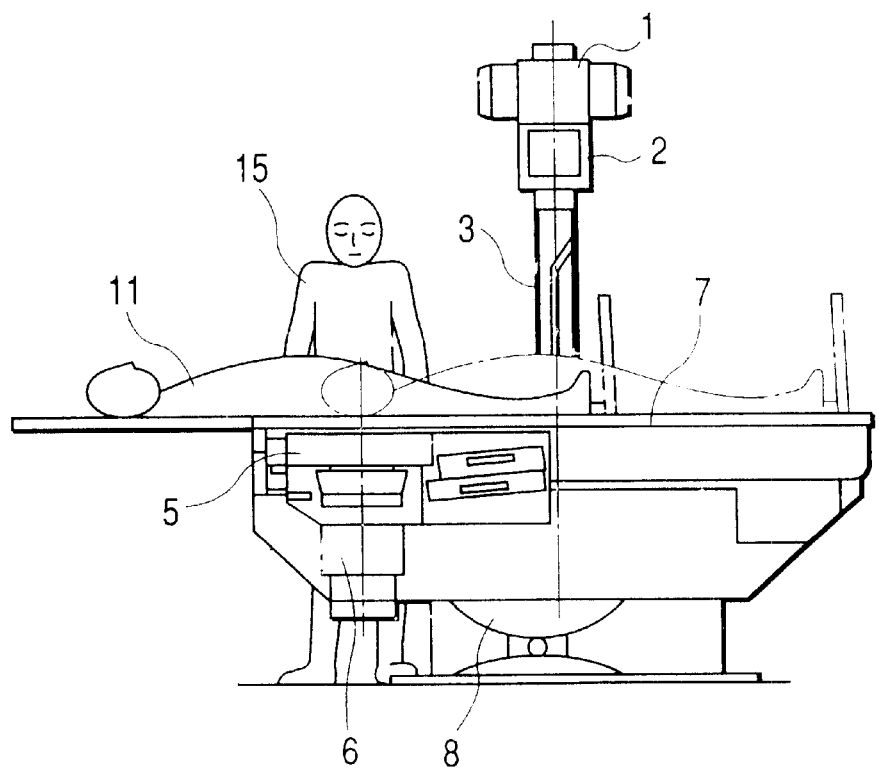
FIG. 2B is a side view showing a state in which the operator approaches from the back side of the X-ray fluoroscopic and radiographic apparatus of the present invention.
Figure 3:
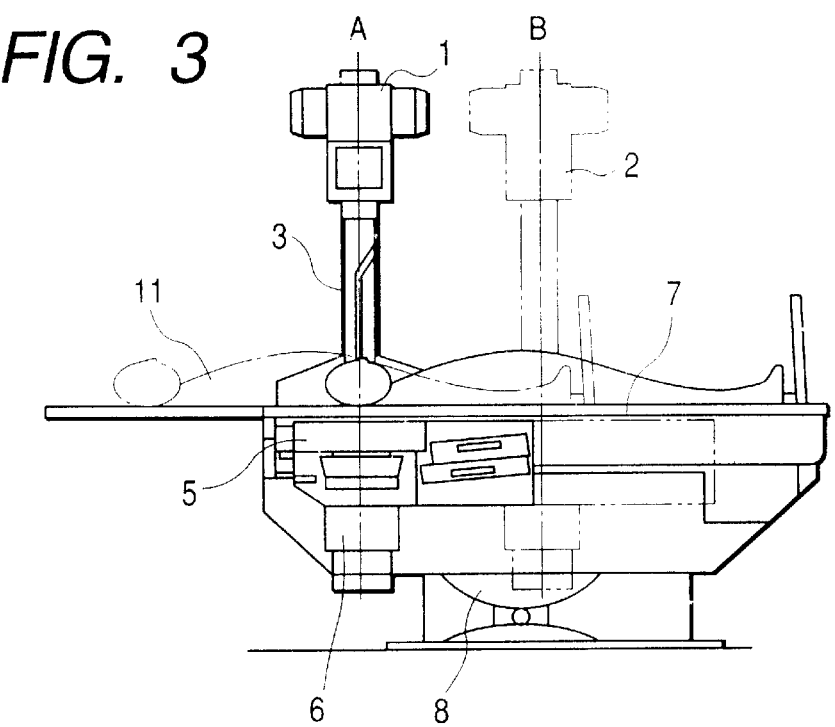
FIG. 3 is a view showing a related art over-tube type X-ray fluoroscopic and radiographic apparatus.
Figure 4:
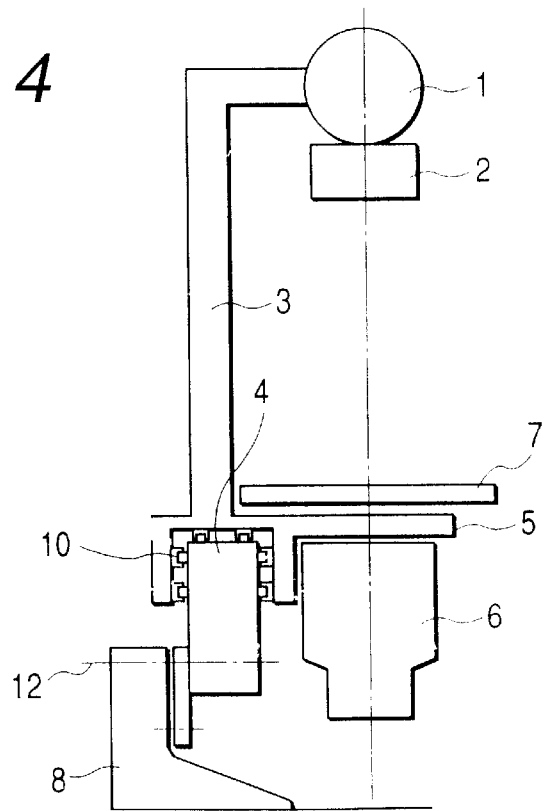
FIG. 4 is a view showing a section of a movement mechanism of a X-ray tube and an image receiving system on the related art X-ray fluoroscopic and radiographic apparatus.

Next, operation of the present X-ray fluoroscopic and radiographic apparatus will be explained referring to FIGS. 2A and 2B. FIGS. 2A and 2B shows a state in which the operator 15 approaches the table top board 7 from the back side of the X-ray fluoroscopic and radiographic apparatus. FIG. 2A is an upper face view, and FIG. 2B is a side view.

First, the X-ray fluoroscopic and radiographic apparatus is set at a horizontal posture. Since the mechanism is composed in such a manner that the X-ray tube 1 and the image receiving system 5 are moved independently from each other, a focal position of the X-ray tube 1 and a tube axis of the image intensifier 6 of the image receiving systems are made to coincide with each other by a controller. Then, X-rays are irradiated from the X-ray tube 1, and an X-ray image formed on a monitor is adjusted in a necessary field of view by the collimator 2. Next, the subject person 11 is put on the table top board 7. Then, X-rays are irradiated again. While observing an X-ray fluoroscopic image formed on the monitor, the operator 15 operates a handle on a control panel of the controller and moves the table top board 7 in the direction of X-Y so that a target portion of the subject person 11 can be positioned at the center on the monitor. At this time, X-ray spot radiography is conducted if necessary.

X-rays are turned off. Depending upon a portion to be diagnosed, marking is made by an illuminating lamp in the target portion on a body surface of the subject person 11. Then, the table top board 7 is moved to a position close to the support column 3 above the main frame 4, and the support column 3 supporting the X-ray tube 1 is moved to a lower side (that is, left-hand side in FIG. 2A) in a longitudinal direction of the table top board 7. At this moment, a space occupied by the support column 3 becomes open. Therefore, it is possible for the operator 15 to approach a position very close to the table top board 7 from the back side of the apparatus. Therefore, in addition to the X-ray fluoroscopic diagnosis, it is possible to conduct other diagnoses such as an endoscope diagnosis and ultrasonic wave diagnosis at the same time.

In the X-ray fluoroscopic and radiographic apparatus, the image receiving system 5 can approach a position distant from an end of the upper side (head portion of the subject person) of the table top board 7, for example, by 38 cm. The operator 15 approaches a front side or the back side of the table top board 7 and conducts an endoscope inspection while monitoring a fluoroscopic image of the head portion of the subject person with the help of an assistant or nurse. Alternatively, the urinary organ inspection (radiography of the kidney and urethra system with a contrast medium) is conducted as follows. While legs of the subject person are arranged on the upper side of the table top board 11, a nurse approaching the table top board 7 injects a contrast medium into the vein of the subject person, and an X-ray inspection engineer conducts a spot-radiography at regular intervals. In order to conducts those inspections, it is necessary for the operator 15, assistant, nurse and X-ray inspection engineer to prepare for the inspection of the subject person 11 around him. Therefore, on this X-ray fluoroscopic and radiographic apparatus, it is possible to make a space when the support column 3 is moved in the longitudinal direction of the table top board 7. Further, it is possible to move the back side portion of the table top board 7 to a position close to the support column above the main frame 4. Therefore, the operator 15 can come to an end of the table top board 7 to conduct the inspection work.

The X-ray fluoroscopic and radiographic apparatus of the present invention is composed as described above. The support column for holding the X-ray tube is held on a side of the main frame, and the support column and the image receiving system are mechanically connected with each other and moved in the longitudinal direction of the table top board, or alternatively the support column and the image receiving system are independently moved in the longitudinal direction of the table top board. When the support column is moved, a space occupied by the support column becomes open, and further the table top board can be moved to a position close to the support column above the main frame. Therefore, it is possible for the operator to approach an end of the table top board and easily make a diagnosis for the subject person while the operator is being kept in an easy body orientation.

What is claimed is:

1. An apparatus for X-ray fluoroscopy and radiography comprising:
   a table top board;
   a support column for holding an X-ray tube above said table top board;
   an image receiving system for holding an image receiving device and being placed on a bottom of said table top board;
   a main frame for holding said support column and said image receiving system so that said support column and said image receiving system can be moved in a longitudinal direction of said table top board, said main frame having a top side, a first lateral side, and a second, opposite lateral side,
   wherein said support column is movably secured to the first lateral side of said main frame and said image receiving system is movably secured to the second lateral side of said main frame.

2. The apparatus for X-ray fluoroscopy and radiography according to claim 1, wherein said support column and said image receiving system are mechanically independently held and moved along said first and second sides of said main frame.

3. The apparatus for X-ray fluoroscopy and radiography according to claim 2, wherein said support column is held by a linear guide formed on the first side of the main frame.

4. The apparatus for X-ray fluoroscopy and radiography according to claim 1, wherein said support column is held by a linear guide formed on the first side of the main frame.

5. The apparatus for X-ray fluoroscopy and radiography according to claim 1, further comprising:
   a drive mechanism for driving said support column along said main frame in the longitudinal direction of said table top board.

6. The apparatus for X-ray fluoroscopy and radiography according to claim 2, wherein said drive mechanism includes a motor, a gear, and a rack.

7. The apparatus for X-ray fluoroscopy and radiography according to claim 5, wherein said drive mechanism includes a motor, a chain, and a sprocket.

8. The apparatus for X-ray fluoroscopy and radiography according to claim 1, wherein said table top board is adapted to move laterally toward said support column so as to cover said top side of said main frame.

9. An apparatus for X-ray fluoroscopy and radiography comprising:
   a table top board;
   a support column for holding an X-ray tube above said table top board;

an image receiving system for holding an image receiving device and being placed on a back of said table top board;

a main frame for holding said support column and said image receiving system so that said support column and said image receiving system can be moved in a longitudinal direction of said table top board, wherein said support column is mechanically held on a side of said main frame which is opposite to a side on which said image receiving system is held, and, wherein said support column and said image receiving system are mechanically independently held and moved on both sides of said main frame.

10. The apparatus for X-ray fluoroscopy and radiography according to claim 9, wherein said support column is held by a linear guide formed on the side of the main frame.

11. The apparatus for X-ray fluoroscopy and radiography according to claim 10, further comprising:

a drive mechanism for driving said support column along said main frame in the longitudinal direction of said table top board.

12. The apparatus for X-ray fluoroscopy and radiography according to claim 11, wherein said drive mechanism includes a motor, a gear, and a rack.

13. The apparatus for X-ray fluoroscopy and radiography according to claim 11, wherein said drive mechanism includes a motor, a chain, and a sprocket.

14. The apparatus for X-ray fluoroscopy and radiography according to claim 9, further comprising:

a drive mechanism for driving said support column along said main frame in the longitudinal direction of said table top board.

15. The apparatus for X-ray fluoroscopy and radiography according to claim 14, wherein said drive mechanism includes a motor, a gear, and a rack.

16. The apparatus for X-ray fluoroscopy and radiography according to claim 14, wherein said drive mechanism includes a motor, a chain, and a sprocket.

* * * * *

UNITED STATES PATENT AND TRADEMARK OFFICE
CERTIFICATE OF CORRECTION

PATENT NO.   : 6,669,365 B2
DATED        : December 30, 2003
INVENTOR(S)  : Iinuma It is certified that error appears in the above-identified patent and that said Letters Patent is hereby corrected as shown below:

<u>Column 6,</u>
Line 54, delete "claim 2" and insert -- claim 5 --.

Signed and Sealed this

Twenty-second Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,669,365 B2
DATED : December 30, 2005
INVENTOR(S) : Iinuma

It is certified that error appears in the above-identified patent and that said Letters Patent is hereby corrected as shown below:

Column 6,
Line 54, delete "claim 2" and insert -- claim 5 --.

Signed and Sealed this

Ninth Day of November, 2004

JON W. DUDAS
*Director of the United States Patent and Trademark Office*